United States Patent
Feucht et al.

(10) Patent No.: US 6,821,926 B1
(45) Date of Patent: Nov. 23, 2004

(54) CARBAMOYL TRIAZOLINONE BASED HERBICIDE

(75) Inventors: Dieter Feucht, Monheim (DE); Peter Dahmen, Neuss (DE); Mark Wilhelm Drewes, Langenfeld (DE); Rolf Pontzen, Leichlingen (DE); Mathias Kremer, Burscheid (DE); Klaus-Helmut Müller, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 79 days.

(21) Appl. No.: 10/130,127

(22) PCT Filed: Nov. 7, 2000

(86) PCT No.: PCT/EP00/10975

§ 371 (c)(1),
(2), (4) Date: May 14, 2002

(87) PCT Pub. No.: WO01/37652

PCT Pub. Date: May 31, 2001

(30) Foreign Application Priority Data

Nov. 19, 1999 (DE) .......................................... 199 55 662

(51) Int. Cl.$^7$ ....................... A01N 43/53; A01N 43/54; A01N 25/32

(52) U.S. Cl. ....................... 504/128; 504/129; 504/130; 504/132; 504/136; 504/137; 504/139

(58) Field of Search ................................ 504/128, 129, 504/130, 132, 134, 136, 137, 139, 103

(56) References Cited

U.S. PATENT DOCUMENTS

| | | | |
|---|---|---|---|
| 5,021,080 A | 6/1991 | Müller et al. .................. 71/92 |
| 5,082,490 A | 1/1992 | Müller et al. .................. 71/92 |
| 5,183,932 A | 2/1993 | Müller et al. ................ 560/330 |
| 5,194,084 A | 3/1993 | Findeisen et al. ........... 504/273 |
| 5,194,085 A | 3/1993 | Lindig et al. ................ 504/273 |
| 5,220,032 A | 6/1993 | Müller et al. |
| 5,326,877 A | 7/1994 | Lindig et al. ............. 548/263.8 |
| 5,356,865 A | 10/1994 | Müller et al. ................ 504/273 |
| 5,399,704 A | 3/1995 | Müller et al. ............. 548/263.8 |
| 5,461,149 A | 10/1995 | Lindig et al. ............. 548/263.8 |
| 5,516,749 A | 5/1996 | Müller et al. ................ 504/273 |
| 5,541,337 A | 7/1996 | Müller et al. ............. 548/263.8 |
| 5,625,073 A | 4/1997 | Lindig et al. ................ 548/263 |
| 5,652,372 A | 7/1997 | Müller et al. ................ 548/263 |
| 5,672,713 A | 9/1997 | Müller et al. ............. 548/263.8 |
| 6,040,271 A | 3/2000 | Thielert et al. ............. 504/134 |
| 6,455,469 B1 * | 9/2002 | Crosby et al. .............. 504/127 |
| 6,649,760 B2 * | 11/2003 | Andree et al. .............. 544/310 |
| 6,683,027 B2 * | 1/2004 | Baltruschat et al. ........ 504/128 |

FOREIGN PATENT DOCUMENTS

| | | |
|---|---|---|
| DE | 196 35 080 | 3/1998 |
| EP | 0 362 633 | 4/1990 |
| EP | 0 612 474 | 8/1994 |

OTHER PUBLICATIONS

*Database Chemabs (Online) Chemical Abstracts Service, Columbus, Ohio, US; B.D. Philbrook et al.;" BAY MKH 3586—a new herbicide for broad spectrum week control in corn (maize) and sugar cane" retrieved from STN–INTERNATIONAL, accession No. 132:1334546 CA XP002162539 abstract & Brighton Conf.—Weeds, Bd. 1, 1999, Seiten 29–34.

Weeds, (month unavailable) 1967, pp. 20–22, "Calculating Synergistic and Antagonistic Responses of Herbicide Combinations" by S. R. Colby.

* cited by examiner

Primary Examiner—Sabiha Qazi
(74) Attorney, Agent, or Firm—Richard E. L. Henderson; John E. Mrozinski, Jr.

(57) ABSTRACT

The invention provides synergistic active compound combinations which are comprised of a carbamoyltriazolinone and at least one herbicidally active compound. The combinations of the present invention find use in controlling plant growth, including weeds.

3 Claims, No Drawings

CARBAMOYL TRIAZOLINONE BASED HERBICIDE

FIELD OF THE INVENTION

The invention relates to new herbicidal, synergistic active compound combinations composed of known carbamoyltriazolinones on the one hand and of known, herbicidally active compounds on the other hand and which can be used particularly successfully for controlling weeds.

BACKGROUND OF THE INVENTION

Carbamoyltriazolinones, being broad-range herbicides, are the subject-matter of a series of patent applications (cf. EP-A 294 666, EP-A 370 293, EP-A 391 187, EP-A 398 096, EP-A 399 294, EP-A 415 196, EP-A 477 646). However, the known carbamoyltriazolinones show a series of gaps with regard to their action.

A series of herbicidal active compound combinations based on N-aryl-uracils has also been disclosed already (cf. DE-A-19 635 060, DE-A-19 635 074). Again, however, the properties of these active compound concentrations are not satisfactory in all respects.

DETAILED DESCRIPTION OF THE INVENTION

Surprisingly, it has now been found that a series of known active compounds from the carbamoyltriazolinone series, used jointly with known herbicidally active compounds from various classes of substances, show pronounced synergistic effects with regard to the action against weeds and can be employed especially advantageously as broad-range combination products for controlling monocotyledonous and dicotyledonous weeds in crops of useful plants such as, for example, in barley, maize, rice, soya beans, sunflowers, wheat and sugar cane, but also for the semi- and nonselective control of monocotyledonous and dicotyledonous weeds.

The invention relates to herbicidal compositions, characterized by an effective Content of an active compound combination comprising (a) a carbamoyltriazolinone of the general formula (I)

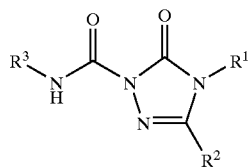

(I)

in which
R¹ represents hydrogen, hydroxyl, amino, or in each case optionally substituted alkyl, alkenyl, alkinyl, alkoxy, alkenyloxy, alkinyloxy, alkylamino, alkenylamino, alkenylamino, alkylideneamino, dialkylamino, cycloalkyl, cycloalkylalkyl, aryl or arylalkyl, R² represents in each case optionally substituted alkyl, alkenyl, alkinyl, alkoxy, alkenyloxy, alkinyloxy, alkylthio, alkenylthio, alkinylthio, alkylamino, alkenylamino, alkinylamino, dialkylamino, cycloalkyl, cycloalkyloxy, cycloalkylalkyl, aryl, aryloxy, arylthio, arylamino or arylalkyl, and R³ represents in each case optionally substituted alkyl, alkenyl, alkinyl, cycloalkyl, cycloalkylalkyl, arylalkyl, arylalkenyl or arylalkinyl, ("active compounds of group 1")
and
(b) one or more compounds from a second group of herbicides containing the active compounds mentioned hereinbelow:

sodium 5-(2-chloro-4-trifluoromethyl-phenoxy)-2-nitrobenzoate (acifluorfen-sodium), 1H-1,2,4-triazol-3-amine (amitrole), 2-[2,4-dichloro-5-(2-propinyloxy)-phenyl]-5,6,7,8-tetrahydro-1,2,4triazolo-[4,3-a]-pyridin-3 (2H)one (azafenidin), N-(4,6-dimethoxy-pyrimidin-2-yl)-N'-[1-methyl-4-(2-methyl-2H-tetrazol-5-yl)-1H-pyrazol-5-ylsulphonyl]urea (azimsulfuron), N-benzyl-2-(4-fluoro-3-trifluoromethyl-phenoxy)-butanamide (beflubutamid), 4-chloro-2-oxo-3(2H)-benzothiazoleacetic acid (benazolin), N-butyl-N-ethyl-2,6-dinitro-4-trifluoromethyl-benzenamine (benfluralin), N-(4,6-dimethoxy-pyrimidin-2-yl)-N'-(2-methoxycarbonyl-phenyl-methylsulphonyl)-urea (bensulfuron), methyl 2-[2-[4-(3,6-dihydro-3-methyl-2,6-dioxo-4-trifluoromethyl-1(2H)-pyrimidinylphenoxymethyl]-5-ethyl-phenoxy-prop-anoate (benzfendizone), 3-(2-chloro-4-methylsulfonyl-benzoyl)-4-phenylthio-bicyclo-[3.2.1]-oct-3-en-2-one (benzobicyclon), ethyl N-benzoyl-N-(3,4-dichloro-phenyl)-DL-alaninate (benzoylprop-ethyl), [1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), N,N-diethyl-3-(2,4,6-trimethyl-phenylsulfonyl)-1H-1,2,4-triazole-1-carboxamide (cafenstrole), 2-[1-[(3-chloro-2-propenyl )-oxy-imino]-propyl]-3-hydroxy-5-(tetrahydro-2H-pyran-4-yl)-2-cyclohexen-1-one (caloxydim, tepraloxydim), N-(4-chloro-6-methoxy-pyrimidin-2-yl)-N'-(2-ethoxycarbonyl-phenylsulfonyl)-urea (chlorimuron-ethyl), ethyl 2-chloro-3-[2-chloro-5-(1,3,4,5, 6,7-hexahydro-1,3-dioxo-2H-isoindol-2-yl)-phenyl]-2-propanoate (cinidon-ethyl), 2-[1-[2-(4-chloro-phenoxy)-propoxyaminobutyl]-5-(tetrahydro-2H-thiopyran-3-yl)-1,3-cyclohexanedione (clef-oxydim), (E,E)-(+)-2-[2-[1-[[(3-chloro-2-propenyl)-oxy]-imino]-propyl]-3-hydroxy-2-cyclohexen-1-one (clethodim), 2-(1-ethoximinobutyl)-3-hydroxy-5-(tetrahydro-2H-thiopyran-3-yl)-2-cyclohexen-1-one (cycloxydim), butyl (R)-2-[4-(4-cyano-2-fluoro-phenoxy)-phenoxy]-propanoate (cyhalofop-butyl), N-(2,6-dichloro-phenyl)-5-ethoxy-7-fluoro-1,2,4-triazolo-[1,5-c]-pyrimidine-2-sulphonamide (diclosulam), 2-[1-[(3,5-difluoro-phenyl)-amino-carbonyl-hydrazono]-ethyl]-pyridine-3-carboxylic acid (di-flufenzopyr), S-(1-methyl-1-phenyl-ethyl) 1-piperidine-carbothioate (dimepiperate), (S)-2-chloro-N-(2,4-dimethyl-3-thienyl) N-(2-methoxy-1-methyl-ethyl)-acetamide (dimethenamid-P), 2-[2-(3-chloro-phenyl)-oxiranylmethyl]-2-ethyl-1H-indene-1,3(2H)-dione (epropodan), (R)-ethyl 2-[4-(6-chloro-benzoxazol-2-yloxy)-phenoxy-propanoate (fenoxaprop-P-ethyl), 4(2-chloro-phenyl)-N-cyclohexyl-N-ethyl-4,5-dihydro-5-oxo-1H-tetrazole-1-carboxamide (fentrazamide), N-(2,6-difluoro-phenyl)-8-fluoro-5-methoxy-[1,2,4]-triazolo-(1,5-c]-pyrimidine-2-sulphonamide (florasulam), butyl (R)-2-[4-(5-trifluoromethyl-pyridin-2-yl-oxy)-phenoxy]-propanoate (fluazifop, -butyl, -P-butyl), i-propyl 5-(4-bromo-1-methyl-5-trifluoromethyl-1H-pyrazol-3-yl)-2-chloro-4-fluoro-benzoate (fluazolate), the sodium salt of 4,5-dihydro-3-methoxy-4-methyl-5-oxo-N-[(2-trifluoromethoxy-phenyl)-sulphonyl]-1-H-1,2,4-triazole-1-carboxamide (flucarbazone-sodium), ethyl [2-chloro-4-fluoro-5-(5-methyl-6-oxo-4-trifluoromethyl-1(6H)-pyridazinyl)-phenoxy]-acetate (flufenpyr), 2-[7-fluoro-3,4-dihydro-3- oxo-4-(2-propinyl)-2H-1,4-benzoxazin-6-yl]-4,5,6,7-tetrahydro-1H-isoindole-1,3-dione (flumioxazin), 2-[4-chloro-2-fluoro-5-[(1-methyl-2-propinyl)-oxy]-phenyl]-4,5,6,7-tetrahydro-1H-isoindole-1,3(2H)-dione (flumipropyn), 3-chloro-4-chloromethyl-1-(3-trifluoromethyl-phenyl)-2-pyrrolidinone (fluorochloridone), the sodium salt of N-(4,6-dimethoxy-pyrimidin-2-yl)-N'-(3-methoxycarbonyl-6-trifluoromethyl-pyridin-2-yl-sulfonyl)-urea (flupyrsulfuron-methyl-sodium), 5-(2-chloro-4-trifluoromethyl-phenoxy)-N-methylsulfonyl-2-nitro-benzamide (fomesafen), 2-[[[[(4,6-dimethoxy-2-pyrimidinyl)-amino]-carbonyl]-amino]-sulphonyl]-4-formylamino-N,N-dimethyl-benzamide (foramsulfuron), (R)-2-[4-(3-chloro-5-trifluoromethyl-pyridin-2-yl-oxy)-phenoxy]-propanoic acid (and its methyl, -2-ethoxyethyl and butyl esters) (haloxyfop, -methyl, -P-methyl, -ethoxyethyl, -butyl), the sodium salt of N-(4-methoxy-6-methyl-1,3,5-triazin-2-yl)-N'-(5-iodo-2-methoxycarbonyl-phenylsulphonyl)-urea (iodosulfuron-methyl-sodium), (4-chloro-2-methylsulphonyl-phenyl)-(5-cyclopropyl-isoxazol4-yl)-methanone (isoxachlonole), 2-[2-[4-[3,5-dichloro-2-pyridinyl)-oxy]-phenoxy]-1-oxo-propyl]-isoxazolidine (isoxapyrifop), (2-ethoxy-1-methyl-2-oxo-ethyl) 5-(2chloro-4-trifluoromethyl-phenoxy)-2-nitro-benzoate (lactofen), 2-(2-benzothiazolyloxy)-N-methyl-N-phenyl-acetamide (mefenacet), methyl 2-[[[[(4,6-dimethoxy-2-pyrimidinyl)-amino]-carbonyl]-amino]-sulphonyl]-4-[[(methylsulphonyl)-amino]-methyl]-benzoate (mesosulfuron), 2-(4-methylsulphonyl-2-nitro-benzoyl)-1,3-cyclohexanedione (mesotrione), 4-amino-3-methyl-6-phenyl-1,2,4-triazin-5(4H)-one (metamitron), (S)-2-chloro-N-(2-ethyl-6-methyl-phenyl)-N-(2-methoxy-1-methyl-ethyl)acetamide (S-metolachlor), S-(2-chloro-benzyl) N,N-diethyl-thiocarbamate (orbencarb), 4-dipropylamino-3,5-dinitro-benzenesulphonamide (oryzalin), 3-[2,4-dichloro-5-(2-propinyloxy)phenyl]-5-(t-butyl)-1,3,4-oxadiazol-2(3H)-one (oxadi-argyl), 3-[2,4-dichloro-5-(1-methyl-ethoxy)-phenyl]-5-(t-butyl)-1,3,4-oxadiazol-2(3H)-one (oxadiazon), 3-[1-(3,5-dichloro-phenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethyl-benzene (oxyfluorfen), 2-(2,2-difluoro-ethoxy)-N-(5,8-dimethoxy[1,2,4]triazolo[1,5-c]pyrimidin-2-yl)-6-trifluoromethyl-benzenesulphonamide (penoxsulam), 2-chloro-N-(2-ethoxy-ethyl)-N-(2-methyl-1-phenyl-1-propenyl)-acetamide (pethoxamid), N-(4-fluoro-phenyl)-6-(3-trifluoromethyl-phenoxy)-pyridine-2-carboxamide (picolinafen), 1-chloro-N-[2-chloro-4-fluoro-5-[(6S,7aR)-6-fluoro-tetrahydro-1,3-dioxo-1H-pyrrolo[1,2]imidazol-2(3H)-yl]-phenyl]-methanesulphonamide (profluazol), N-(3,4-dichloro-phenyl)-propanamide (propanil), (R)-2-[[(1-methyl-ethylidene)-amino]-oxy]-ethyl]2-[4-(6-chloro-2-quinoxalinyloxy)-phenoxy]-propanoate (propaquizafop), 2-chloro-N-(2-ethyl-6-methyl-phenyl)-N-[(1-methyl-ethoxy)-methyl]-acetamide (propisochlor), the sodium salt of methyl 2-[[[(4,5-dihydro-4-methyl-5-oxo-3-propoxy-1H-1,2,4-triazol-1-yl)-carbonyl]-amino]-sulfonyl]-benzoate (procarbazone-sodium), 1-(3-chloro-4,5,6,7-tetrahydro-pyrazolo[1,5-a]pyridin-2-yl)-5-(methyl-2-propinylamino)-1H-pyrazole-4-carbonitrile (pyrazogyl), diphenylmethanone O-[2,6-bis-(4,6-dimethoxy-pyrimidin-2-yl-oxy)-benzoyl]-oxime (pyribenzoxim), 6-chloro-3-phenyl-pyridazin-4-ol (pyridatol), 7-[(4,6-dimethoxy-2-pyrimidinyl)-thio]-3-methyl-1(3H)-isobenzofuranone (pyriftalide), methyl 2-(4,6-dimethoxy-pyrimidin-2-yl-oxy)-benzoate (pyriminobac-methyl), sodium 2-chloro-6-(4,6-dimethoxy-pyrimidin-2-ylthio)-benzoate (pyrithiobac-sodium), 3,7-dichloro-quinolin-8-carboxylic acid (quinchlorac), 2-[4-(6-chloro-2-quinoxalinyloxy)-phenoxy]-propanoic acid (and its ethyl and tetrahydro-2-furanyl-methyl esters) (quizalofop, -ethyl, -P-ethyl, -P-tefuryl), 2-(1-ethoximinobutyl)-5-(2-ethylthiopropyl)-3-hydroxy-2-cyclohexen-1-one (sethoxydim), methyl 2-difluoromethyl-5-(4,5-dihydro-thiazol-2yl)-4-(2-methyl-propyl)-6-trifluoromethyl-pyridine-3-carboxylate (thiazopyr), (3,5,6-trichloro)-pyridin-2-yl-oxy-acetic acid (triclopyr), the sodium salt of N-[[(4,6-dimethoxy-2-pyrimidinyl)-amino-]carbonyl]-3-(2,2,2-trifluoro-ethoxy)-2-pyridinesulphonamide (trifloxysulfuron), N-[4-dimethylamino-6-(2,2,2-trifluoro-ethoxy)-1,3,5-triazin-2-yl]-N'-(2-methoxycarbonyl-phenylsulphonyl)-urea (triflusulfuron-methyl), N-(4-methoxy-6-trifluoromethoxy-1,3,5-triazin-2-yl)-N'-(2-trifluoromethyl-phenyl-sulphonyl)-urea (tritosulfuron), N-[[(4,6-dimethoxy-2-pyrimidinyl)-amino]-carbonyl]-3-(N-methyl-N-methylsulphonyl-amino])-2-pyridinesulphonamide (cf. WO-A-92/10660), methyl 2-[[[[(4,6-dimethoxy-2-pyrimidinyl)-amino]-carbonyl]-amino]-sulphonyl]-4-[[(methylsulphonyl)-amino]methyl]-benzoate (cf. DE-A-43 35 297), 4-[4,5-dihydro-4-methyl-5-oxo-(3-trifluoromethyl)-1H-1,2,4-triazol-1-yl]-2-[(methylsulphonyl)amino]-5-fluoro-benzenecarbothioamide (cf. WO-A-95/30661), ("active compounds of group 2"),
and, if appropriate,
(c) a compound which improves crop plant tolerance, from amongst the following group of compounds:

4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinoxalin-8-oxy-acetate (cloquintocet-mexyl), α-(cyano-methoximino)-phenylacetonitrile (cyometrinil), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), N-(4-methyl-phenyl)-N'-(1-methyl-1-phenyl-ethyl)-urea (dymron), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazol-ethyl), phenylmethyl 2chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900). ethyl 4,5-dihydro5,5-phenyl-3-isoxazole carboxylate (isoxadifen-ethyl), diethyl-1-(2,4-dichlorophenyl)-4,5-dihydro-5-methyl-1H-pyrazole-3,5-dicarboxylate (mefenpyr-diethyl) 2-dichloromethyl-2-methyl-1,3-dioxolane (MG-191), 1,8-naphthalenedicarboxylic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), methyl 1-(2-chloro-phenyl)-5-phenyl-1H-pyrazole-3-carboxylate and N-(2-methoxy-benzoyl)-4-[(methylamino-carbonyl)-amino]-benzenesulphonamide ("active compounds of group 3").
Preferred meanings of the radicals mentioned in the above formula (I) are illustrated hereinbelow.

$R^1$ preferably represents hydrogen, hydroxyl, amino, or represents alkyl, alkenyl, alkinyl, alkoxy, alkenyloxy, alkinyloxy, alkylamino, alkenylamino, alkinylamino, alkylideneamino or dialkylamino, each of which has up to 6 carbon atoms and each of which is optionally substituted by halogen or cyano, or represents cycloalkyl, cycloalkylalkyl, each of which has 3 to 6 carbon atoms in the cycloalkyl groups and, if appropriate, 1 to 4 carbon atoms in the alkyl group and each of which is optionally substituted by halogen, cyano or $C_1$–$C_4$-alkyl, or represents phenyl or phenyl-$C_1$–$C_4$-alkyl, each of which is optionally substituted by halogen, cyano, $C_1$–$C_4$-alkyl or $C_1$–$C_4$-alkoxy.

$R^2$ preferably represents alkyl, alkenyl, alkinyl, alkoxy, alkenyloxy, alkinyloxy, alkylthio, alkenylthio, alkinylthio, alkylamino, alkenylamino, alkinylamino or dialkylamino, each of which has up to 6 carbon atoms and each of which is optionally substituted by halogen, cyano, $C_1$–$C_4$-alkoxy or $C_1$–$C_4$-alkylthio, or represents cycloalkyl, cycloalkyloxy or cycloalkylalkyl, each of which has 3 to 6 carbon atoms in the cycloalkyl groups and, if appropriate, 1 to 4 carbon atoms in the alkyl group and each of which is optionally substituted by halogen, cyano or $C_1$–$C_4$-alkyl, or represents phenyl, phenoxy, phenylthio, phenylamino or phenyl-$C_1$–$C_4$-alkyl, each of which is optionally substituted by halogen, cyano, $C_1$–$C_4$-alkyl or $C_1$–$C_4$-alkoxy.

$R^3$ preferably represents alkyl, alkenyl or alkinyl, each of which has up to 10 carbon atoms and each of which is optionally substituted by halogen, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylamino or di-($C_1$–$C_4$-alkyl)amino, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen, cyano or $C_1$–$C_4$-alkyl, or represents phenyl-$C_1$–$C_6$-alkyl, phenyl-$C_2$–$C_6$-alkenyl or phenyl-$C_2$–$C_6$-alkinyl, each of which is optionally substituted by halogen, cyano, $C_1$–$C_4$-alkyl or $C_1$–$C_4$-alkoxy.

$R^1$ especially preferably represents hydrogen, hydroxyl, amino, or represents methyl, ethyl, n- or i-propyl, n-, i-, s- or t-butyl, propenyl, butenyl, propinyl or butinyl, methoxy, ethoxy, n- or i-propoxy, n-, i-, s- or t-butoxy, propenyloxy, butenyloxy, propinyloxy or butinyloxy, methylamino, ethylamino, n- or i-propylamino, n-, i-, s- or t-butylamino, propenylamino, butenylamino, propinylamino or butinylamino, ethylideneamino, propylideneamino, butylideneamino, dimethylamino or diethylamino, each of which is optionally substituted by fluorine, chlorine or cyano, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl or benzyl, each of which is optionally substituted by fluorine, chlorine, bromine, cyano, methyl, ethyl, n- or i-propyl, n-, i-, s- or t-butyl, methoxy or ethoxy.

$R^2$ especially preferably represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n or i-propylthio, n-, i-, s- or t-butylthio, propenylthio, butenylthio, propinylthio, butinylthio, methylamino, ethylamino, n- or i-propylamino, n-, i-, s- or t-butylamino, propenylamino, butenylamino, propinylamino, butinylamino, dimethylamino or diethylamino, each of which is optionally substituted by fluorine, chlorine, cyano, methoxy, ethoxy, n- or i-propoxy, methylthio, ethylthio, n- or i-propylthio, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl or cyclohexylmethyl, each of which is optionally substituted by fluorine, chlorine, bromine, cyano, methyl, ethyl, n- or i-propyl, or represents phenyl, phenoxy, phenylthio, phenylamino or benzyl, each of which is optionally substituted by fluorine, chlorine, bromine, cyano, methyl, ethyl, n- or i-propyl, n-, i-, s- or t-butyl, methoxy or ethoxy.

$R^3$ especially preferably represents methyl, ethyl, n- or i-propyl, n-, i-, s- or t-butyl, propenyl, butenyl, pentenyl, hexenyl, propinyl, butinyl, pentinyl or hexinyl, each of which is optionally substituted by fluorine, cyano, methoxy, ethoxy, n- or i-propoxy, n-, i-, s- or t-butoxy, methylthio, ethylthio, n- or i-propylthio, n-, i-, s-, or t-butylthio, methylsulphinyl, ethylsulphinyl, methylsulphonyl, ethylsulphonyl, methylamino, ethylamino, n- or i-propylamino, n-, i-, s- or t-butylamino, dimethylamino, diethylamino, dipropylamino or dibutylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl, n- or i-propyl, or represents benzyl, phenylethyl, phenylpropyl, phenylbutyl, phenylethenyl, phenylpropenyl, phenylbutenyl, phenylethinyl, phenylpropinyl or phenylbutinyl, each of which is optionally substituted by fluorine, chlorine, bromine, cyano, methyl, ethyl, n- or i-propyl, n-, i-, s- or t-butyl, methoxy or ethoxy.

$R^1$ very especially preferably represents hydrogen, amino, or represents methyl, ethyl, n- or i-propyl, propenyl, butenyl, propinyl or butinyl, methoxy, ethoxy, n- or i-propoxy, propenyloxy or propinyloxy, each of which is optionally substituted by fluorine or chlorine, or represents methylamino, ethylamino, n- or i-propylamino, propenylamino or propinylamino, dimethylamino or diethylamino, or represents cyclopropyl or cyclopropylmethyl, each of which is optionally substituted by fluorine, chlorine, cyano or methyl.

$R^2$ very especially preferably represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylamino, ethylamino, n- or i-propylamino, n-, i-, s- or t-butylamino, propenylamino, butenylamino, propinylamino, butinylamino, dimethylamino or diethylamino, each of which is optionally substituted by fluorine, chlorine, cyano, methoxy, ethoxy, methylthio or ethylthio, or represents cyclopropyl, cyclopropyloxy or cyclopropylmethyl, each of which is optionally substituted by fluorine, chlorine, cyano or methyl.

$R^3$ very especially preferably represents methyl, ethyl, n- or i-propyl, n-, i-, s- or t-butyl, propenyl, butenyl, pentenyl, hexenyl, propinyl, butinyl, pentinyl or hexinyl, each of which is optionally substituted by fluorine, cyano, methoxy, ethoxy, n- or i-propoxy, methylthio, ethylthio, n- or i-propylthio, methylsulphinyl, ethylsulphinyl, methylsulphonyl, ethylsulphonyl, methylamino, ethylamino, n- or i-propylamino, dimethylamino or diethylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl, n- or i-propyl, or represents benzyl, phenylethyl, phenylpropyl, phenylbutyl, phenylethenyl, phenylpropenyl, phenylbutenyl, phenylethinyl, phenylpropinyl or phenylbutinyl, each of which is optionally substituted by fluorine, chlorine, bromine, cyano, methyl, ethyl, n- or i-propyl, n-, i-, s- or t-butyl, methoxy or ethoxy.

Examples which may be mentioned individually of the compounds of the formula (I) to be used as components according to the invention in mixtures are:
4-amino-5-methyl-2-(1,1-dimethyl-ethyl-aminocarbonyl)-2,4-dihydro-3H-1,2,4-triazol-3-one, 4-amino-5-ethyl-2-(1,1-dimethyl-ethyl-aminocarbonyl)-2,4-dihydro-3H-1,2,4-triazol-3-one, 4-amino-5-n-propyl-2-(1,1-dimethyl-ethyl-aminocarbonyl)-2,4-dihydro-3H-1,2,4-triazol-3-one, 4-amino-5-i-propyl-2-(1,1-dimethyl-ethyl-aminocarbonyl)-2,4-dihydro-3H-1,2,4-triazol-3-one, 4-amino-5-methoxy-2-(1,1-dimethyl-ethyl-aminocarbonyl)-2,4-dihydro-3H-1,2,4-triazol-3-one, 4-amino-5-ethoxy-2-(1,1-dimethyl-ethyl-aminocarbonyl)-2,4-dihydro-3H-1,2,4-triazol-3-one, 4-amino-5-methyl-2-(2-fluoro-1,1-dimethyl-ethyl-aminocarbonyl)-2,4-dihydro-3H-1,2,4-triazol-3-one, 4-amino-5-ethyl-2-(2-fluoro-1,1-dimethyl-ethyl-aminocarbonyl)-2,4-dihydro-3H-1,2,4-triazol-3-one, 4-amino-5-n-propyl-2-(2-fluoro-1,1-dimethyl-ethyl-aminocarbonyl)-2,4-dihydro-3H-1,2,4-triazol-3-one, 4-amino-5-i-propyl-2-(2-fluoro-1,1-dimethyl-ethyl-aminocarbonyl)-2,4dihydro-3H-1,2,4-triazol-3-one, 4-amino-5-methoxy-2-(2-fluoro-1,1-dimethyl-ethyl-aminocarbonyl)-2,4-dihydro-3H-1,2,4-triazol-3-one, 4-amino-5-ethoxy-2-(2-fluoro-1,1-dimethyl-ethyl-aminocarbonyl)-2,4-dihydro-3H-1,2,4-triazol-3-one, 4-amino-5-methyl-2-(2-chloro-1,1-dimethyl-ethyl-aminocarbonyl)-2,4-dihydro-3H-1,2,4-triazol-3-one, 4-amino-5-ethyl-2-(2-chloro-1,1-dimethyl-ethyl-aminocarbonyl)-2,4-dihydro-3H-1,2,4-triazol-3-one, 4-amino-5-n-propyl-2-(2-chloro-1,1-dimethyl-ethyl-aminocarbonyl)-2,4-dihydro-3H-1,2,4-triazol-3-one, 4-amino-5-i-propyl-2-(2-chloro-1,1-dimethyl-ethyl-amino-carbonyl)-2,4-dihydro-3H-1,2,4-triazol-3-one, 4-amino-5-methoxy-2-(2-chloro-1,1-dimethylethyl-aminocarbonyl)-2,4-dihydro-3H-1,2,4-triazol-3-one, 4-amino-5-ethoxy-2-(2-chloro-1,1-dimethyl-ethyl-aminocarbonyl)-2,4-dihydro-3H-1,2,4-triazol-3-one, 4-amino-5-i-propyl-2-i-propyl-aminocarbonyl-2,4-dihydro-3H-1,2,4-triazol-3-one, 4-amino-5-dimethylamino-2-(1,1-dimethyl-ethyl-aminocarbonyl)-2,4-dihydro-3H-1,2,4-triazol-3-one, 4-amino-5-dimethylamino-2-(2-fluoro-1,1-dimethyl-ethyl-aminocarbonyl)-2,4-dihydro-3H-1,2,4-triazol-3-one, 4-amino-5-dimethylamino-2-(2-chloro-1,1-dimethyl-ethyl-aminocarbonyl)-2,4-dihydro-3H-1,2,4-triazol-3-one and 4-methyl-5-methoxy-2-(1,1-dimethyl-ethyl-aminocarbonyl)-2,4-dihydro-3H-1,2,4-triazol-3-one.

The compound 4-amino-5-(1-methyl-ethyl)-2-(1,1-dimethyl-ethyl-aminocarbonyl)-2,4-dihydro-3H-1,2,4-triazol-3-one—in accordance with Chem. Abstracts also to be termed 4-amino-N-(1,1-dimethyl-ethyl)-4,5-dihydro-3-(1-methyl-ethyl)-5-oxo-1H-1,2,4-triazole-1-carboxamide (CAS-Reg. No.: 129909-90-6, Compound (I-1) of the use examples, proposed common name: "amicarbazone")—is particularly emphasized as component of the formula (I) in the mixture.

The compounds of the formula (I) are described in the abovementioned patent applications or patent specifications.

In accordance with their chemical structure, the active compounds of group 2 can be assigned to the following classes of active compounds:

Amides (for example, picolinafen, propanil), arylheterocycles (for example, azafenidin, benzfendizone, butafenacil-allyl, cinidon-ethyl, fluazolate, flumioxazin, oxadiazon, oxadiargyl, profluazol, pyraflufen-ethyl, pyridatol, 4-[4,5-dihydro-4-methyl-5-oxo-(3-trifluoromethyl)-1H-1,2,4-triazol-1-yl]-2-[(ethylsulphonyl)amino]-5-fluorobenzenecarbothioamide), aryloxyphenoxypropionates (for example cyhalofop-butyl, fenoxaprop-P-ethyl, fluazifop-P-butyl, haloxyfop-P-methyl, quizalofop-P-ethyl), carboxylic acid derivatives (for example tyriclopyr), chloroacetamides (for example dimethenamid-P, S-metolachlor, propisochlor), cyclohexanediones (for example butroxydim, clefoxydim, cycloxydim, sethoxydim), dinitroanilines (for example benfluralin, oryzalin), diphenylethers (for example acifluorfen-sodium, fomesafen, lactofen, oxyfluorfen), isoxazoles (for example, isoxachlortole), oxyacetamides (for example mefenacet), pyridines (for example thiazopyr), pyrimidinyl (thio)benzoates (for example pyribenzoxim, pyriminobac-methyl, pyrithiobac-sodium), sulphonyl ureas (for example azimsulfuron, bensulfuron, chlorimuron-ethyl, flupyrsulfuron-methyl-sodium, foramsulfuron, iodosulfuron-methyl-sodium, trifloxysulfuron, triflusulfuron-methyl, tritosulfuron), tetrazolinones (for example fentrazamide), thiocarbamates (for example dimepiperate), triazinones (for example metamitron), triazoles (for example amitrole), triazolinones (for example flucarbazone-sodium, procarbazone-sodium) triazolopyrimidines (for example diclosulam, florasulam), triketones (for example mesotrione).

The following may be emphasized in particular as components for mixtures amongst active compounds of group 2:
azafenidin, butafenacil-allyl, dimethenamid-P, fenoxaprop-P-ethyl, mesotrione, S-metolachlor.

The compositions according to the invention preferably comprise one or two active compounds of group 1, one to three active compounds of group 2 and, if appropriate, one active compound of group 3.

In particular, the compositions according to the invention comprise one active compound of group 1, one or two active compounds of group 2 and, if appropriate, one active compound of group 3.

Examples of the active compound combinations according to the invention which may be mentioned are:
Amicarbazone+butafenacil-allyl, amicarbazone+mesotrione, amicarbazone+fenoxaprop-P-ethyl+mefenpyr-diethyl, amicarbazone+flucarbazone-sodium, amicarbazone+flucarbazone-sodium+mefenpyr-diethyl, amicarbazone+procarbazone-sodium, amicarbazone+procarbazone-sodium+mefenpyr-diethyl, amicarbazone+dimethenamid-P, amicarbazone+S-metolachlor, amicarbazone+S-metolachlor+benoxacor.

Surprisingly, it has now been found that the above-defined active compound combinations of the carbamoyltriazolinones of the formula (I) and the abovementioned active compounds of group 2 exhibit a particularly high herbicidal activity combined with essentially good crop plant tolerance and can be used for the selective control of monocotyledonous and dicotyledonous weeds in a variety of crops, in particular in maize, but additionally also in cotton, sunflowers, soya beans, potatoes, sugar cane, wheat, barley and rice, and that they can also be used for the semi- and nonselective control of monocotyledonous and dicotyledonous weeds.

Surprisingly, the herbicidal activity of the active compound combinations according to the invention of compounds of the abovementioned groups 1 and 2 considerably exceeds the total of the action of the individual active compounds.

Thus, a synergistic effect is present which could not have been predicted, not just a complementation of action. The new active compound combinations are well tolerated in a variety of crops, also effecting good control of weeds which are usually difficult to control. Thus, the new active compound combinations are a valuable enrichment of the herbicides.

The synergistic effect of the active compound combinations according to the invention is particularly highly pronounced in certain concentration ratios. However, the weight ratios of the active compounds in the active compound combinations may be varied within substantial ranges. In general, 0.01 to 1000 pans by weight, preferably 0.02 to 500 parts by weight, especially preferably 0.05 to 100 parts by weight, of active compound of group 2 are used per part by weight of active compound of the formula (I).

The following may be particularly emphasized as components in mixtures from amongst active compounds of group 3:

1-Methyl-hexyl 5-chloro-quinoxalin-8-oxy-acetate (cloquintocet-mexyl), ethyl 4,5-dihydro-5,5-diphenyl-3-isoxazolecarboxylate (isoxadifen-ethyl) and diethyl 1-(2,4-dichloro-phenyl)4,5-dihydro-5-methyl-1H-pyrazole-3,5-dicarboxylate (mefenpyr-diethyl) for improving the tolerance in cereals, and 4-dichloroacetyl-1-oxa-4-aza-spiro [4.5]-decane (AD-67), 1-dichloroacetyl-hexahydro-3,3,8a-trimethylpyrrolo[1,2-a]-pyrimidin-6(2H)-one (BAS-145138), 4-dichloroacetyl-3,4-dihydro-3-methyl-2H-1,4-benzoxazine (benoxacor), 2,2-dichloro-N,N-di-2-propenyl-acetamide (dichlormid), 3-dichloroacetyl-5-(2-furanyl)-2,2-dimethyl)-oxazolodine (furilazole, MON-13900), 3-dichloroacetyl-2,2,5-trimethyl-oxazolidine (R-29148) for improving the tolerance in maize.

It must be considered as surprising that, from amongst a multiplicity of known safeners or antidotes capable of antagonizing the harmful effect of a herbicide on the crop plants, it is precisely the abovementioned compounds of group 3 which are capable of virtually completely making up for the harmful effect, on the crop plants, of active compounds of the formula (I) and their salts, if appropriate also in combination with one or more of the abovementioned active compounds of group 2, without adversely affecting the herbicidal efficacy towards the weeds.

The advantageous effect of the crop plant tolerance of the active compound combinations according to the invention is also particularly highly pronounced. However, the weight ratios of the active compounds in the active compound combinations may be varied within substantial ranges. In general, 0.001 to 1000 parts by weight, preferably 0.01 to 100 parts by weight, especially preferably 0.1 to 10 parts by weight, of active compound of group 3 are used per part by weight of active compound of the formula (I) or mixtures thereof with active compounds of group 2.

All plants and plant parts can be treated in accordance with the invention. Plants are to be understood as meaning in the present context plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights. Plant parts are to be understood as meaning all aerial and subterranean plant parts and organs of the plants such as shoot, leaf, flower and root, examples which may be mentioned being leaves, needles, stalks, flowers, fruiting bodies, fruits, seeds, roots, tubers and rhizomes. The plant parts also include vegetative and generative propagation material, for example cuttings, tubers, rhizomes, offsets and seeds.

The treatment according to the invention of the plant and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

Amongst the plants obtained by biotechnological and recombinant methods, or by combining these methods, plants which are emphasized arc those which tolerate so-called 4-HPPD, EPSP and/or PPO inhibitors, such as, for example, Acuron plants.

The active compounds according to the invention can be used, for example, in the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compound combinations according to the invention is in no way restricted to these genera, but also extends in the same manner to other plants.

The active compound combinations to be used in accordance with the invention can be employed not only in conventional cultivation methods (suitably placed row crops) in plantation crops (for example grapevines, fruit, citrus) and in industrial plants and railtracks, on paths and squares, but also for stubble treatment and in the minimum tillage method. They are furthermore suitable as dessicants (haulm killing in, for example, potatoes) or as defoliants (for example in cotton). They are furthermore suitable for use on non-crop areas. Other fields of application are nurseries, forests, grassland and the production of ornamentals.

The active compound combinations can be converted into the customary formulations such as solutions, emulsions, wettable powders, suspensions, powders, dusts, pastes, soluble powders, granules, suspo-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants and/or foam formers.

In the case of the use of water as an extender, organic solvents can, for example, also be used as cosolvents. The following are essentially suitable as liquid solvents: aromatics such as xylene, toluene, or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Solid carriers which are suitable are:

for example ammonium salts and ground natural minerals such as kaolins, clays, talc, chalk, quartz, attapulgite, montmorillonite or diatomaceous earth, and ground synthetic materials such as highly-dispersed silica, alumina and silicates; suitable solid catalysts for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compounds, preferably between 0.5 and 90%.

The active compound combinations according to the invention are generally applied in the form of ready mixes. However, the active compounds contained in the active compound combinations may also be applied in the form of individual formulations which are mixed upon use, that is, in the form of tank mixes.

The new active compound combinations, as such or in their formulations, may furthermore also be used as a mixture with other known herbicides, again with ready mixes or tank mixes being possible. A mixture with other known active compounds such as fungicides, insecticides, acaricides, nematicides, bird repellants, growth substances, plant nutrients and soil conditioners is also possible. It may furthermore be advantageous for specific applications, in particular for the post-emergence method, to incorporate into the formulations plant-tolerated mineral or vegetable oils (for example the commercial product "Oleo DuPont 11E") or ammonium salts such as, for example, ammonium sulphate or ammonium thiocyanate, as further additives.

The new active compound combinations can be used as such, in the form of their formulations or the use forms which can be prepared from these formulations by further dilution, such as ready-to-use solutions, suspensions, emulsions, powders, pastes and granules. Application is effected in the customary manner, for example by pouring, spraying, atomizing, dusting or broadcasting.

The active compound combinations according to the invention can be applied before and after emergence of the plants, that is to say pre- and post-emergence. They may also be incorporated into the soil prior to sowing.

The good herbicidal action of the new active compound combinations can be seen from the examples which follow. While the individual active compounds show weaknesses with regard to their herbicidal action, the combinations all show a herbicidal action which exceeds a simple sum of actions.

A synergistic effect in herbicides is always present when the herbicidal action of the active compound combination exceeds the action of the active compounds when applied individually.

The expected action for a given combination of two herbicides can be calculated as follows (cf. COLBY. S. R.: "Calculating synergistic and antagonistic responses of herbicide combinations". Weeds 15, Pages 20–22. 1967):

If

X=damage by herbicide A (active compound of the formula I) at an application rate of p kg/ha and Y=% damage by herbicide B (active compound of the formula II) at an application rate of q kg/ha and E=the expected damage of herbicides A+B at an application rate of p +q kg/ha, then $E=X+Y-(X*Y/100)$.

If the actual damage exceeds the calculated value, the combination has a superadditive effect, that is to say a synergistic effect.

It can be seen from the use examples hereinbelow that the found herbicidal action of the active compound combinations according to the invention exceeds the calculated value, that is to say that the new active compound combinations have a synergistic effect.

USE EXAMPLES

Customary formulations of the respective active compounds were used. Butafenacil was employed as Inspire® 100 EC, azafenidin as an 80 WG formulation and the compound of the formula (I-1) as a 70 WG formulation. The active compounds were used to prepare an aqueous spray mixture with 0.1% of Renex-36 as additive.

Example A

Pre-emergence/greenhouse

Seeds of the test plants are sown in standard soil. After 24 hours, the test compound or the combination of test compounds, is sprayed onto the soil surface in such a manner as to apply the amount of active compound per unit area desired in each case. The concentration of the spray mixture is chosen so that the desired amounts of active compound desired are applied in 500 l of water per ha.

After the spray application, the plant containers are placed in the greenhouse under constant light and temperature conditions.

After approximately 3 weeks, the degree of damage of the crop plants is scored in % damage in comparison with the development of the untreated control.

The figures denote:

0%=no damage (as untreated control)

100%=Total destruction/damage

Active compounds, application rates, test plants and results can be seen from the tables which follow, the terms used in the tables having the following meanings:

a.i.=active ingredient

TABLE A-1

|  | Application rate g ai/ha | Alopecurus observed | Alupecurus calculated* |
|---|---|---|---|
| Compound (I-1) | 125 | 0 | |
| Butafenacil | 2 | 0 | |
|  | 0.5 | 0 | |
| Compound (I-1) + Butafenacil | 125 + 2 | 70 | 0 |
|  | 125 + 0.5 | 60 | 0 |

TABLE A-2

|  | Application rate g ai/ha | Digitaria observed | Digitaria calculated* |
|---|---|---|---|
| Compound (I-1) | 125 | 40 | |
| Butafenacil | 1 | 20 | |
|  | 0.5 | 20 | |
| Compound (I-1) + Butafenacil | 125 + 1 | 90 | 52 |
| MKH 3586 + Butafenacil | 125 + 0.5 | 90 | 52 |

*Data calculated using Colby's formula

TABLE A-3

|  | Application rate g ai/ha | Setaria observed | Setaria calculated* |
|---|---|---|---|
| Compound (I-1) | 125 | 0 | |
| Butafenacil | 2 | 0 | |
|  | 0.5 | 0 | |
| Compound (I-1) + Butafenacil | 125 + 2 | 80 | 0 |
|  | 125 + 0.5 | 70 | 0 |

TABLE A-4

|  | Application rate g ai/ha | Abutilon observed | Abutilon calculated* |
|---|---|---|---|
| Compound (I-1) | 60 | 50 | |
| Butafenacil | 2 | 30 | |
| Compound (I-1) + Butafenacil | 60 + 2 | 95 | 65 |

*Data calculated using Colby's formula

TABLE A-5

|  | Application rate g ai/ha | Cassia observed | Cassia calculated* |
|---|---|---|---|
| Compound (I-1) | 60 | 30 | |
| Butafenacil | 0.5 | 0 | |
| MKH 3586 + Butafenacil | 60 + 0.5 | 100 | 30 |

TABLE A-6

|  | Application rate g ai/ha | Datura observed | Datura calculated* |
|---|---|---|---|
| Compound (I-1) | 60 | 50 | |
| Butafenacil | 2 | 30 | |
| Compound (I-1) + Butafenacil | 60 + 2 | 100 | 65 |

*Data calculated using Colby's formula

TABLE A-7

|  | Application rate g ai/ha | Galium observed | Galium calculated* |
|---|---|---|---|
| Compound (I-1) | 125 | 80 | |
| Butafenacil | 1 | 0 | |
| Compound (I-1) + Butafenacil | 125 + 1 | 100 | 80 |

TABLE A-8

|  | Application rate g ai/ha | Ipomea observed | Ipomea calculated* |
|---|---|---|---|
| Compound (I-1) | 125 | 50 | |
| Butafenacil | 0.5 | 0 | |
| Compound (I-1) + Butafenacil | 125 + 0.5 | 98 | 50 |

*Data calculated using Colby's formula

TABLE A-9

|  | Application rate g ai/ha | Solanum observed | Solanum calculated* |
|---|---|---|---|
| Compound (I-1) | 60 | 90 | |
| Butafenacil | 2 | 0 | |
|  | 1 | 0 | |
|  | 0,5 | 0 | |
| Compound (I-1) + Butafenacil | 60 + 2 | 100 | 90 |
|  | 60 + 1 | 100 | 90 |
|  | 60 + 0,5 | 98 | 90 |

TABLE A-10

|  | Application rate g ai/ha | Xanthium observed | Xanthium calculated* |
|---|---|---|---|
| Compound (I-1) | 125 | 90 |  |
| Butafenacil | 2 | 0 |  |
| Compound (I-1) + Butafenacil | 125 + 2 | 100 | 90 |

*Data calculated using Colby's formula

What is claimed is:

1. A composition comprising a synergistically effective amount of an active compound combination comprising 4-amino-5-(1-methyl-ethyl)-2-(1,1-dimethyl-ethyl-aminocarbonyl)-2,4-dihydro-3H-1,2,4,-triazol-3-one, and

[1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (butafenacil-allyl).

2. A process for the preparation of a herbicidal composition comprising mixing the composition of claim 1 with at least one of extenders and surfactants.

3. A method of controlling plant comprising applying a synergistically, herbicidally effective amount of a composition according to of claim 1 to the plant and/or its locus.

* * * * *